United States Patent
Copmans et al.

(10) Patent No.: US 8,461,341 B2
(45) Date of Patent: Jun. 11, 2013

(54) RESOLUTION OF (±)-METHYL PHENYL[4-[4-[[[4'(TRIFLUOROMETHYL)-2-BIPHENYLYL]CARBONYL]AMINO]PHENYL]-1-PIPERIDINYL]ACETATE

(75) Inventors: Alex Herman Copmans, Lille (BE); Jérôme Albert Joseph Hoet, Braine-l'Alleud (BE); Albert Louis Anna Willemsens, Beerse (BE); Wouter Louis J Couck, Sint-Amandsberg (BE); Joannes Petrus Van Dun, Lille (BE)

(73) Assignee: Janssen Pharmaceutica NV, Beerse (BE)

( * ) Notice: Subject to any disclaimer, the term of this patent is extended or adjusted under 35 U.S.C. 154(b) by 25 days.

(21) Appl. No.: 13/322,575

(22) PCT Filed: May 27, 2010

(86) PCT No.: PCT/EP2010/057319
§ 371 (c)(1),
(2), (4) Date: Nov. 28, 2011

(87) PCT Pub. No.: WO2010/136526
PCT Pub. Date: Dec. 2, 2010

(65) Prior Publication Data
US 2012/0071660 A1    Mar. 22, 2012

(30) Foreign Application Priority Data
May 29, 2009   (EP) .................... 09161460

(51) Int. Cl.
*A61K 31/445* (2006.01)
*C07D 211/32* (2006.01)

(52) U.S. Cl.
USPC .......................................... 546/234; 514/317

(58) Field of Classification Search
None
See application file for complete search history.

(56) References Cited

FOREIGN PATENT DOCUMENTS

| EP | 0142191 B1 | 5/1985 |
|---|---|---|
| WO | WO 02/20501 A2 | 3/2002 |
| WO | WO 02/081460 A1 | 10/2002 |

OTHER PUBLICATIONS

International Search Report relating to International Patent Application No. PCT/EP2010/057319. Date of Mailing of International Search Report: Aug. 18, 2010.
Written Opinion of the International Searching Authority relating to International Patent Application No. PCT/EP2010/057319. Date of Mailing of Written Opinion: Aug. 18, 2010.

*Primary Examiner* — Janet Andres
*Assistant Examiner* — Heidi Reese

(57) ABSTRACT

The present invention relates to a resolution process of (±)-methyl phenyl[4-[4-[[[4'-(trifluoromethyl)-2-biphenylyl]carbonyl]amino]phenyl]-1-piperidinyl]acetate to isolate the MTP (microsomal triglyceride transfer protein) inhibitor methyl (2S)-phenyl[4-[4-[[[4'-(trifluoromethyl)-2-biphenylyl]carbonyl]amino]phenyl]-1-piperidinyl]acetate and an epimerisation procedure for racemizing methyl (2R)-phenyl[4-[4-[[[4'-(trifluoromethyl)-2-biphenylyl]carbonyl]amino]phenyl]-1-piperidinyl]acetate.

13 Claims, No Drawings

RESOLUTION OF (±)-METHYL PHENYL[4-[4-[[[4'(TRIFLUOROMETHYL)-2-BIPHENYLYL]CARBONYL]AMINO]PHENYL]-1-PIPERIDINYL]ACETATE

CROSS REFERENCE TO RELATED APPLICATIONS

This application is the U.S. national stage of Application No. PCT/EP2010/057319, filed May 27, 2010, which application claims priority from EP 09161460.2, filed May 29, 2009.

The present invention relates to a resolution process of (±)-methyl phenyl[4-[4-[[[4'-(trifluoromethyl)-2-biphenylyl]carbonyl]amino]phenyl]-1-piperidinyl]acetate to isolate the MTP (microsomal triglyceride transfer protein) inhibitor methyl (2S)-phenyl[4-[4-[[[4'-(trifluoromethyl)-2-biphenylyl]carbonyl]amino]phenyl]-1-piperidinyl]-acetate and an epimerisation procedure for racemizing methyl (2R)-phenyl [4-[4-[[[4'-(trifluoromethyl)-2-biphenylyl]carbonyl]amino]phenyl]-1-piperidinyl]acetate.

The MTP inhibitor methyl (2S)-phenyl[4-[4-[[[4'-(trifluoromethyl)-2-biphenylyl]-carbonyl]amino]phenyl]-1-piperidinyl]acetate is a small molecule, enterocyte targeted, microsomal triglyceride transfer protein (MTP) inhibitor. This compound is rapidly metabolised in the plasma, yielding very low systemic plasma concentrations, and is designed to inhibit predominantly intestinal MTP resulting in the inhibition of triglyceride absorption after the meals but has limited effects on the liver. It is disclosed in WO-02/20501 for use in the treatment of disorders such as obesity, hyperlipidemia, hypercholesterolemia, hypertriglyceridemia, type 2 diabetes, atherosclerosis and for the reduction of postprandial serum triglyceride plasma levels.

The MTP inhibitor methyl (2S)-phenyl[4-[4-[[[4'-(trifluoromethyl)-2-biphenylyl]-carbonyl]amino]phenyl]-1-piperidinyl]acetate has the following structure and will be referred to as "(S)-Compound A". This compound has been disclosed in international application WO-02/20501 as compound (230) having a specific optical rotation of $[\alpha]_D^{20}=+27.69°$ (c=24.95 mg/5 ml in $CH_3OH$). Therefore this compound has also been named as (+)-phenyl-(4-{4-[(4'-(trifluoromethyl-biphenyl-2-carbonyl)-amino]-phenyl}-piperidin-1-yl)-acetic acid methyl ester.

(S)-Compound A

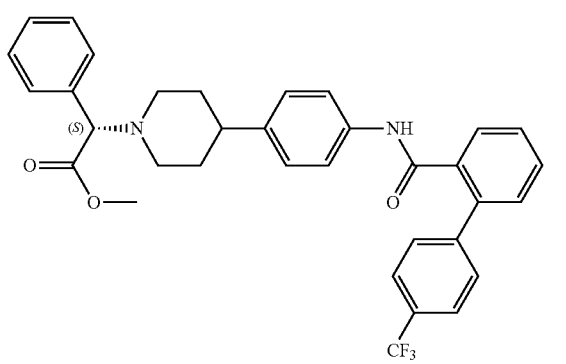

The mirror image of "(S)-Compound A" is methyl (2R)-phenyl[4-[4-[[[4'-(trifluoromethyl)-2-biphenylyl]carbonyl]amino]phenyl]-1-piperidinyl]acetate and is disclosed in WO-02/20501 as compound (229) having a specific optical rotation $[\alpha]_D^{20}$ of −28.86° (c=24.95 mg/5 ml in $CH_3OH$). This compound will be referred to as "(R)-Compound A".

(R)-Compound A

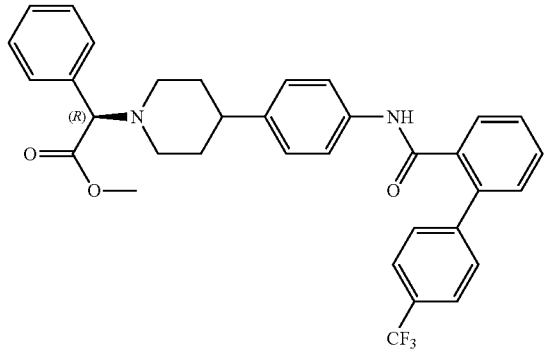

The 1:1 mixture of the enantiomers "(S)-Compound A" and "(R)-Compound A" is denoted the racemate "(±)-Compound A", or with the chemical name (±)-methyl phenyl[4-[4-[[[4'-(trifluoromethyl)-2-biphenylyl]carbonyl]amino]phenyl]-1-piperidinyl]-acetate, which has been disclosed in WO-02/20501 as compound (41) having the following structure:

(±)-Compound A

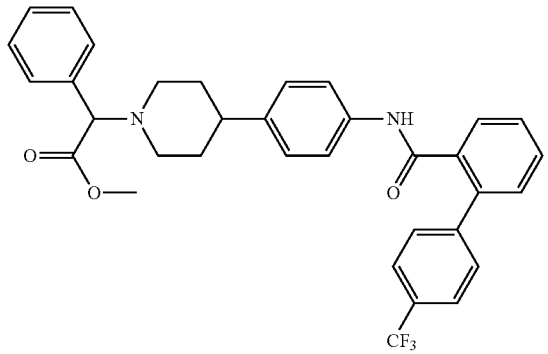

To ensure a sufficient supply of "(S)-Compound A" for clinical development and sales, an efficient process is required which can be carried out on a large, commercial scale.

It is an object of the invention to provide a process for the preparation of methyl (2S)-phenyl[4-[4-[[[4'-(trifluoromethyl)-2-biphenylyl]carbonyl]amino]phenyl]-1-piperidinyl]acetate (i.e. "(S)-Compound A") which is highly efficient (i.e. high yield and high enantiomeric purity in one single step) and which is suitable for operation on a large, commercial scale.

The present invention relates to a process for isolating "(S)-Compound A" by resolving "(±)-Compound A" via the formation of diastereoisomeric salts with the resolving agent (S)-N-[(4-methoxyphenyl)sulfonyl]glutamic acid.

Several chiral acids have been tested as optical resolution agent for the resolution of "(±)-Compound A" and it was unexpectedly found that (S)-N-[(4-methoxy-phenyl)sulfonyl]glutamic acid gave the highest yield of the desired enantiomer "(S)-Compound A" with the highest enantiomeric purity.

The present invention also relates to a process for racemizing "(R)-Compound A" into "(±)-Compound A" which can then be resolved again according to the present invention. This racemisation or epimerisation process is a further object of the present invention and makes it in principal possible to convert the starting "(±)-Compound A" almost quantitatively to the desired enantiomer "(S)-Compound A".

The term "enantiomer" refers to stereoisomer molecules which are non-superimposable mirror images of each other. Enantiomers are typically designated using the stereodescriptors (R) and (S) to describe the absolute configuration in accordance with the Cahn-Ingold-Prelog sequence rules. Stereoisomerism may also be denoted by the direction of which way polarised light is rotated using either (+) or dextrorotatory to indicate a rotation to the right, or (−) or laevorotatory to indicate a rotation to the left.

The term enantiomeric excess (e.e.) is well-known to the person skilled in stereochemistry. For a mixture of (+) and (−) enantiomers, with composition given as the mole or weight fractions of F(+) and F(−) [where F(+)+F(−)=1], the enantiomeric excess for F(*) is defined as F(+)−F(−), and the percent enantiomeric excess as 100*[F(+)−F(−)]. The enantiomeric ratio is defined as the ratio of the percentage of one enantiomer in a mixture to that of the other as, e.g. 80:20.

In particular, the present invention concerns a process for isolating methyl (2S)-phenyl[4-[4-[[[4'-(trifluoromethyl)-2-biphenylyl]carbonyl]amino]phenyl]-1-piperidinyl]acetate or a pharmaceutically acceptable salt thereof from (±)-methyl phenyl[4-[4-[[[4'-(trifluoromethyl)-2-biphenylyl]carbonyl]amino]phenyl]-1-piperidinyl]acetate or an acid addition salt thereof by the consecutive steps of a) mixing (±)-methyl phenyl[4-[4-[[[4'-(trifluoromethyl)-2-biphenylyl]carbonyl]-amino]phenyl]-1-piperidinyl]acetate or an acid addition salt thereof with a suitable amount of (S)-N-[(4-methoxyphenyl)sulfonyl]glutamic acid or an alkali or earth alkaline metal salt thereof in a suitable solvent at an elevated temperature;

b) cooling the mixture of step a) and collecting the precipitated methyl (2S)-phenyl[4-[4-[[[4'-(trifluoromethyl)-2-biphenylyl]carbonyl]amino]phenyl]-1-piperidinyl]-acetate. (S)-N-[(4-methoxyphenyl)sulfonyl]glutamic acid salt; and c) liberating methyl (2S)-phenyl[4-[4-[[[4'-(trifluoromethyl)-2-biphenylyl]carbonyl]-amino]phenyl]-1-piperidinyl]acetate from the said precipitated salt; and optionally converting methyl (2S)-phenyl[4-[4-[[[4'-(trifluoromethyl)-2-biphenylyl]carbonyl]amino]phenyl]-1-piperidinyl]acetate into a pharmaceutically acceptable salt.

The pharmaceutically acceptable addition salts of "(S)-Compound A" as mentioned hereinabove are meant to include the therapeutically active non-toxic acid addition salt forms which "(S)-Compound A" is able to form and which may conveniently be obtained by treating said compound with an appropriate acid. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxy-benzoic), p-aminosalicylic, pamoic and the like.

The acid addition salts of "(±)-Compound A" as mentioned hereinabove may conveniently be obtained by treating said compound with an appropriate acid. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxy-benzoic), p-aminosalicylic, pamoic and the like.

The molar ratio of the resolving agent (S)-N-[(4-methoxyphenyl)sulfonyl]-glutamic acid to the amount of "(±)-Compound A" ranges from 0.5 to 1.1 and in practice typically an amount of 1.05 mol of (S)-N-[(4-methoxyphenyl)sulfonyl] glutamic acid is used to resolve 1 mol of "(±)-Compound A".

The resolving agent (S)-N-[(4-methoxyphenyl)sulfonyl] glutamic acid may also be used in the form of its mono- or dialkali metal or earth alkaline metal salts, in particular the mono- and disodium or potassium salts.

The choice of "(±)-Compound A" or a suitable acid addition salt thereof as well as the choice of the resolving agent (S)-N-[(4-methoxyphenyl)sulfonyl]glutamic acid or a mono- or dialkali metal or earth alkaline metal salt thereof is determined by the nature of the solvent or the solvent mixture used in the crystallisation step.

The solvent or the solvent mixture used in the crystallisation step can be any organic solvent, or mixture, wherein the diastereomeric salt "(S)-Compound A".(S)-N—[(4-methoxyphenyl)sulfonyl]glutamic acid has a low solubility at relatively low temperatures. The solvent or solvent mixture may contain water up to 10% but preferably the solvent or solvent mixture is anhydrous. The following solvents have shown to yield the desired enantiomer "(S)-Compound A" with a high enantiomeric purity: 2-butanone (also known as methyl ethyl ketone or MEK), 4-methyl-2-pentanone (also known as methyl isobutyl ketone or MIK), ethyl acetate and 1-propanol. Mixtures of these solvents can also be used.

Since "(S)-Compound A" has basic properties it may easily be liberated from the diastereomeric salt by treating the latter with an appropriate base, such as, for example, alkali metal or earth alkaline metal carbonates or hydroxides, e.g. sodium carbonate, potassium carbonate, sodium hydroxide and the like, or organic bases such as, for example, triethylamine, N,N-diethylethanamine, pyridine and the like.

A suitable method for liberating "(S)-Compound A" from the diastereomeric salt "(S)-Compound A".(S)-N-[(4-methoxyphenyl)sulfonyl]glutamic acid salt is, for example, dissolving said diastereomeric salt in an organic solvent, optionally at an elevated temperature, until a homogeneous solution is obtained, followed by the addition of an aqueous solution containing an inorganic base such as e.g. sodium hydroxide, sodium carbonate, potassium carbonate or ammonia hydroxide and cooling of the resulting reaction mixture whereby the desired "(S)-Compound A" precipitates.

Another suitable method for liberating "(S)-Compound A" from the diastereomeric salt "(S)-Compound A".(S)-N-[(4-methoxyphenyl)sulfonyl]glutamic acid salt is, for example, by solubilizing the diastereomeric salt in a solvent-system consisting of a water-immiscible organic solvent and a suitable alkaline aqueous medium, e.g. an aqueous sodium hydroxide solution or an aqueous sodium carbonate solution, and extracting the aqueous phase with said water-immiscible organic solvent. The "(S)-Compound A" present in the organic solvent layer may be isolated following art-known procedures.

The (S)-N-[(4-methoxyphenyl)sulfonyl]glutamic acid present in the hereinabove mentioned aqueous phase may be recovered to be used in a subsequent resolution-cycle. Depending upon the particulars of the contemplated resolution process and the solvent used therein the (S)-N-[(4-methoxyphenyl)sulfonyl]glutamic acid may be used as such or converted into a suitable salt form.

A schematic overview of the resolution process of the present invention is given below:

Step a)

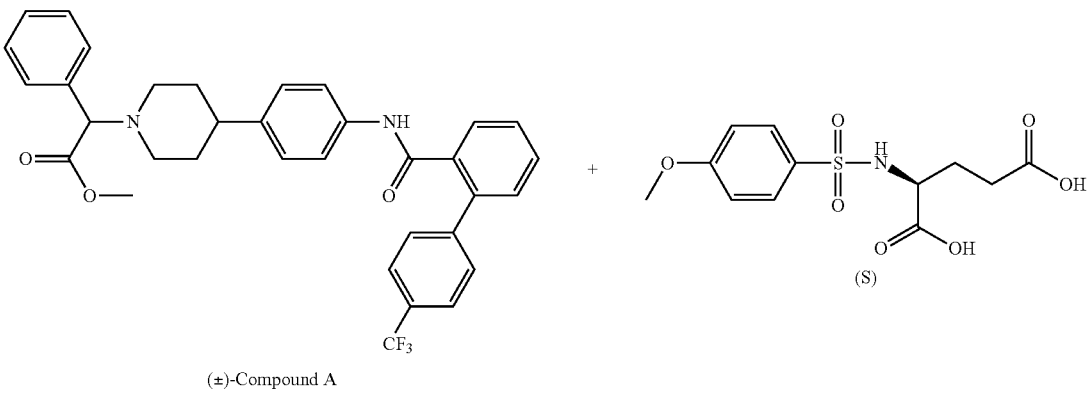

(±)-Compound A

ΔT | suitable organic solvent

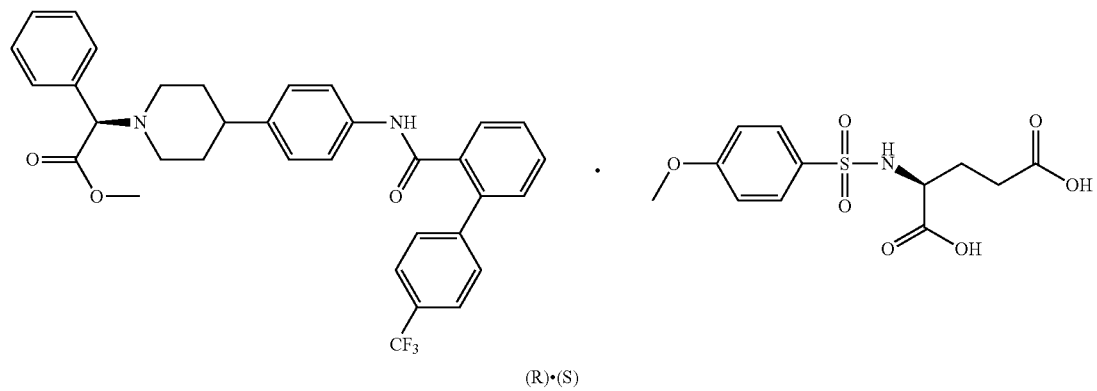

(R)•(S)

+

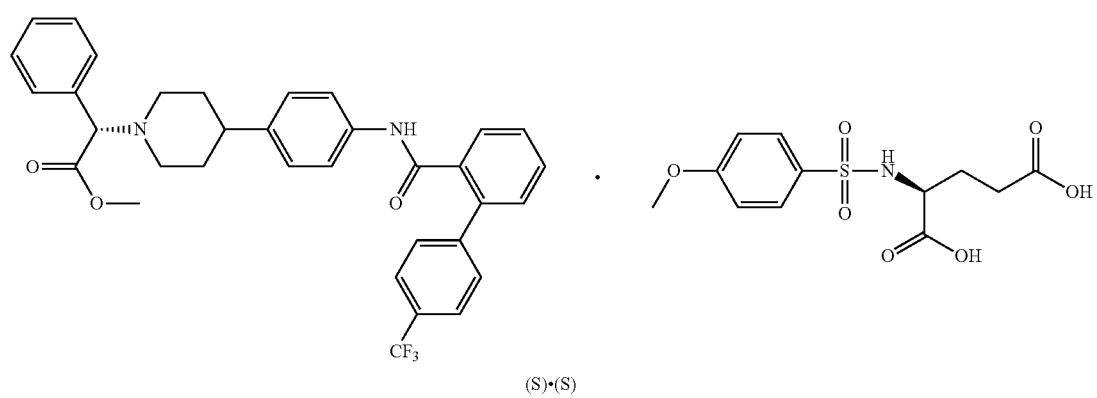

(S)•(S)

In the above overview, the resolving agent used in step a) is (S)-N-[(4-methoxyphenyl)sulfonyl]glutamic acid which has the (S) absolute stereochemistry. "(±)-Compound A" is dissolved in a suitable organic solvent together with the resolving agent (S)-N-[(4-methoxyphenyl)sulfonyl]glutamic acid at an elevated temperature. Two diastereomeric salts are formed in solution: "(R)-Compound A".(S)-N-[(4-methoxyphenyl)sulfonyl]glutamic acid salt with the (R).(S) absolute stereochemistry and the salt "(S)-Compound A".(S)-N-[(4-methoxyphenyl)sulfonyl]-glutamic acid salt with the (S).(S) absolute stereochemistry.

The (R).(S) diastereomeric salt "(R)-Compound A".(S)-N-[(4-methoxy-phenyl)sulfonyl]-glutamic acid has a much higher solubility in the organic solvent than the (S).(S) diastereomeric salt "(S)-Compound A".(S)-N-[(4-methoxyphenyl)sulfonyl]-glutamic acid salt whereby the latter can be collected by precipitation in step b) by lowering the temperature.

Step b)

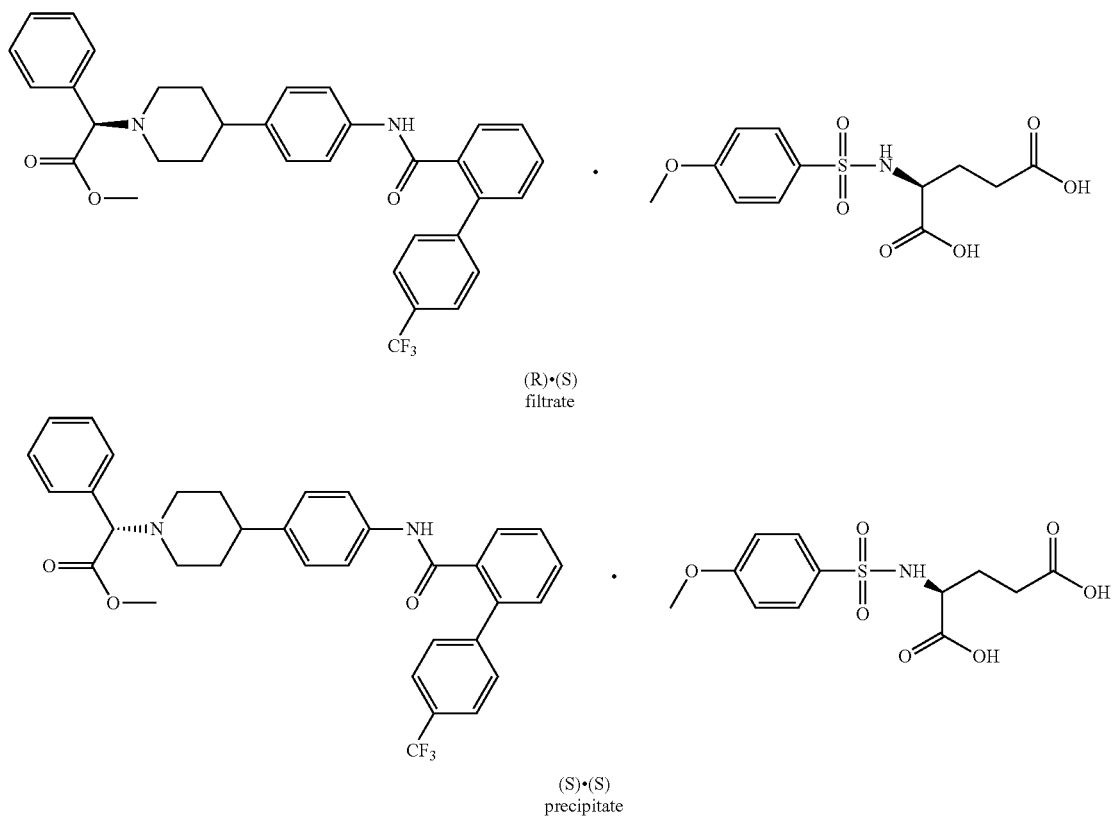

The isolated (S).(S) diastereomeric salt "(S)-Compound A".(S)-N-[(4-methoxyphenyl)sulfonyl]glutamic acid from step b) can be converted into its free base form "(S)-Compound A" by dissolving the (S).(S) diastereomeric salt "(S)-Compound A".(S)-N-[(4-methoxyphenyl)sulfonyl]glutamic acid in an organic solvent, such as e.g. propyleneglycolmonomethylether, at an elevated temperature until a homogeneous solution is obtained, followed by the addition of an aqueous solution containing an inorganic base such as e.g. sodium hydroxide, sodium carbonate, potassium carbonate or ammonia hydroxide, and cooling of the resulting reaction mixture whereby the desired "(S)-Compound A" precipitates.

Step c)

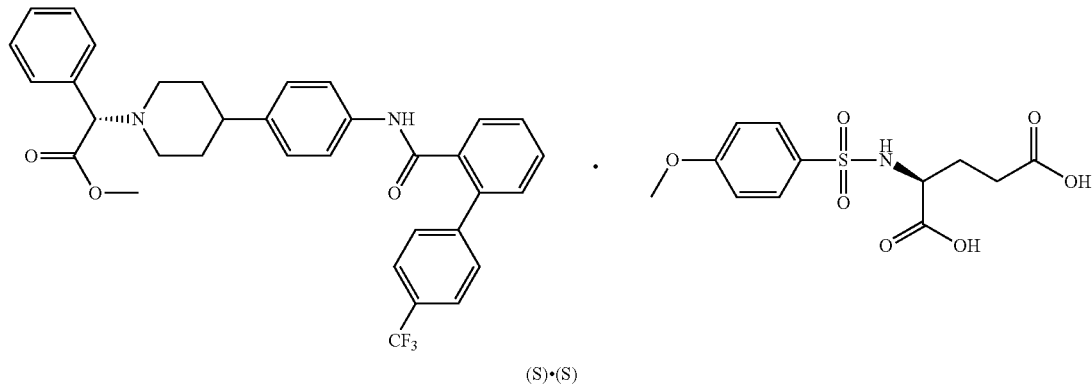

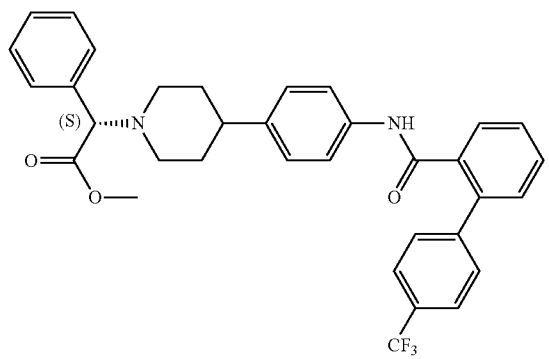

(S)-Compound A

Alternatively, step c) can be performed by dissolving said (S).(S) diastereomeric salt in a solvent-system consisting of a water-immiscible organic solvent and a suitable alkaline aqueous solution, followed by thoroughly mixing the two phases, and extracting the aqueous phase with said water-immiscible organic solvent. The desired "(S)-Compound A" in the organic solvent layer can be isolated following art-known procedures. Suitable water-immiscible organic solvents are e.g. dichloromethane, ethyl acetate, and 2-methyl-tetrahydrofuran.

The temperature conditions for the resolution procedure of the present invention are dependent upon the solvent. For instance when the solvent is 2-butanone, then the following conditions apply:

step a): the temperature ranges between 60° C. and 65° C.,
step b): cooling is in accordance with a a non-linear cooling profile, in particular cooling to 55° C. over 15 minutes, to 17.5° C. over 4 hours and to 17° C. over a period of 1 hour to 16 hours.

When the resolution process is performed in another solvent, the temperature for step a) and the cooling profile for step b) can be determined by the skilled person in order to achieve a highly efficient resolution process (i.e. high yield and high enantiomeric purity in one single step).

Optionally, the optical antipode of the desired enantiomer "(S)-Compound A", i.e. "(R)-Compound A", may be racemized in "(±)-Compound A" which may then be reused in the resolution process with the resolving agent (S)-N-[(4-methoxyphenyl)-sulfonyl]glutamic acid in order to obtain the desired enantiomer "(S)-Compound A".

Racemisation of "(R)-Compound A" can be performed by heating the diastereomeric salt "(R)-Compound A".(S)-N-[(4-methoxyphenyl)sulfonyl]glutamic acid present in the motherliquor of the resolution step b) at an elevated temperature for a prolonged time, optionally at an increased pressure. Under these circumstances, the diastereomeric salt "(R)-Compound A".(S)-N-[(4-methoxyphenyl)sulfonyl]glutamic acid epimerises into a 1:1 mixture of (R).(S) and (S).(S) diastereomeric salts from which the (S).(S) diastereomeric salt can be isolated by precipitation when lowering the temperature of the reaction mixture (in analogy with step b).

Epimerisation

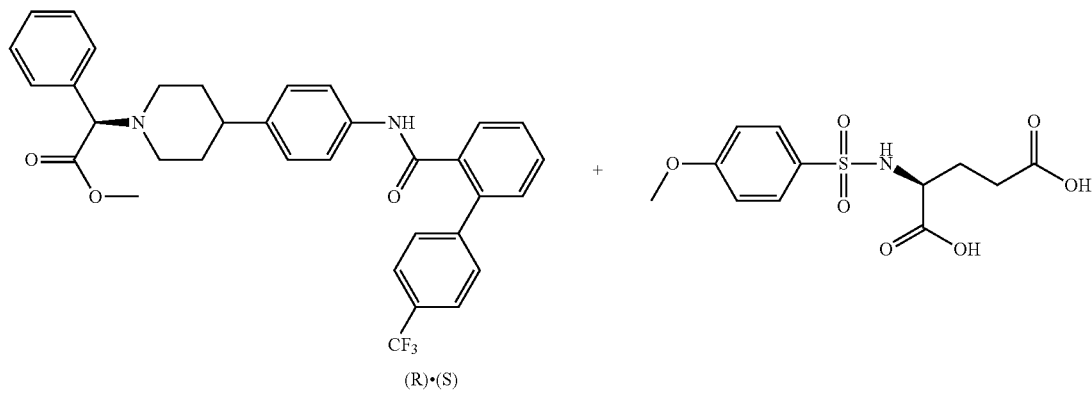

(R)•(S)

ΔT | organic solvent

-continued

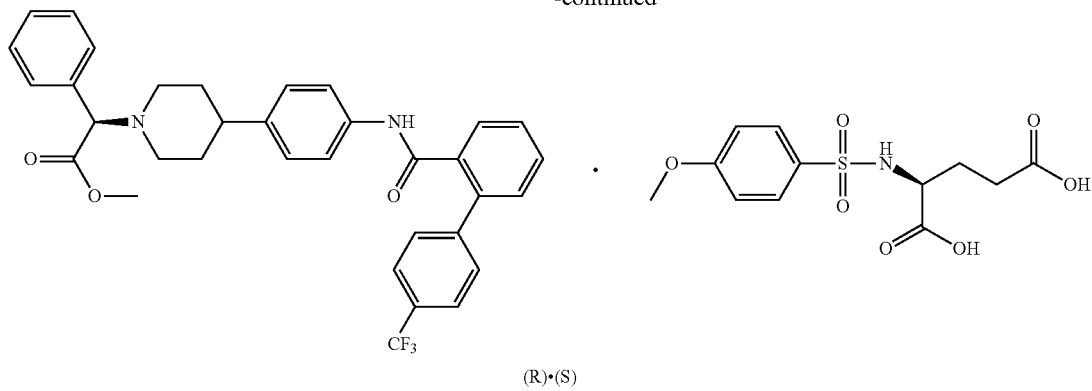

(R)•(S)

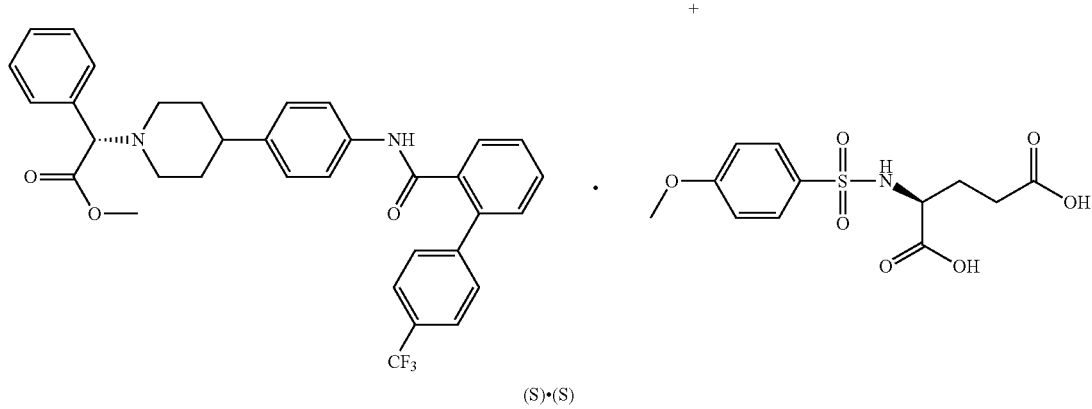

(S)•(S)

Optionally the "(R)-Compound A" may also be racemized in "(±)-Compound A" by dissolving "(R)-Compound A" in a suitable solvent such as, e.g. methanol, ethanol, dimethylformamide in the presence of a strong base such as, e.g. sodium hydride, sodium methoxide or potassium tert-butoxide.

Racemisation

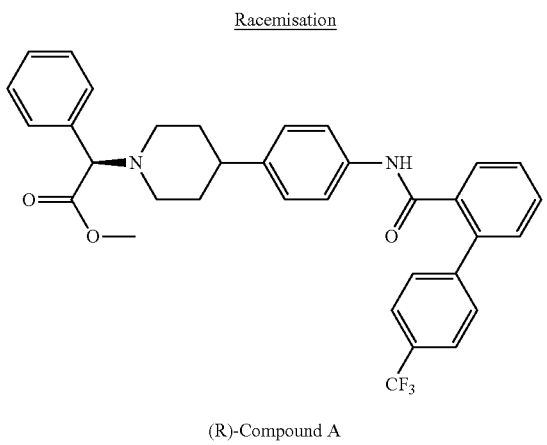

(R)-Compound A strong base ↓

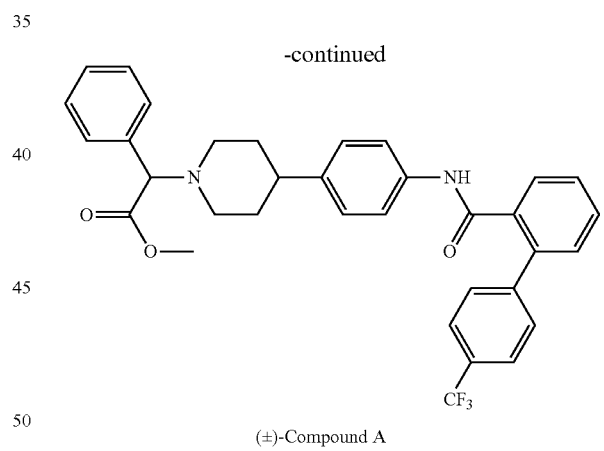

(±)-Compound A

EXPERIMENTAL PART

In the procedures described hereinafter the following abbreviations were used: 'MEK means methyl ethyl ketone (or 2-butanone).

EXAMPLE 1

An aqueous solution of sodium hydroxide (50%, 52 ml) was added to a solution of monosodium (S)-glutamate monohydrate (1 mol) in water (437 ml). The reaction mixture was stirred and the temperature was raised to 35° C.-40° C. 4-Methoxybenzenechloride (1 mol) was added and the reaction mixture was stirred while the pH and the temperature were monitored (exothermic reaction). The temperature of the reaction mixture was kept between 50° C. and 80° C. and in order to keep the pH of the reaction mixture between 8 and 11 an aqueous solution of sodium hydroxide (50%) was added portionwise. After 1 hour, the reaction mixture was cooled to a temperature between 20° C. and 25° C., MEK (1000 ml) was added and the pH was adjusted to pH=1 using a concentrated aqueous hydrochloric acid solution. The organic layer was separated and water was removed by azeotropic distillation until the boiling point of MEK was reached. The residue, i.e. (S)-N-[(4-methoxy-phenyl)sulfonyl] glutamic acid, was diluted with MEK (860 ml).

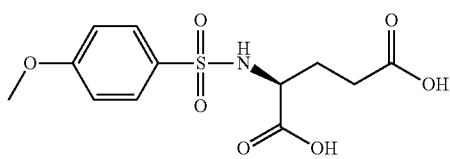

(S)-N-[(4-methoxyphenyl)sulfonyl]glutamic acid
(IUPAC): (S)-2-(4-methoxybenzenesulfonylamino)-pentanedioic acid

EXAMPLE 2

A mixture of "(±)-Compound A" (572 g, 1 mol), MEK (1820 ml) and dicalite (11 g) was heated to a temperature between 60° C. and 65° C. and held for 15 minutes. The mixture was filtered. To the filtrate a solution of (S)-N-[(4-methoxyphenyl)sulfonyl]glutamic acid (1.05 mol) in MEK (903 ml) was added while stirring the reaction mixture. The reaction mixture was cooled to 58° C. over a period of 15 to 20 minutes. An amount of seed crystals of "(S)-Compound A". (S)-N-[(4-methoxyphenyl)sulfonyl]glutamic acid salt (1.37 g), prepared in a separate run, was added and the reaction mixture was cooled according to the following gradient (non-lineair cooling profile):
to 55° C. over 15 minutes
to 17.5° C. over 4 hour The reaction mixture was then stirred for a period of 1 hour up to 16 hours at a temperature of 17° C. The precipitate was filtered off and washed with MEK (280 ml). The product was dried in vacuum, yielding 423.8 g of "(S)-Compound A".(S)-N-[(4-methoxyphenyl)sulfonyl]glutamic acid salt. The filtrate was set aside.

HPLC analysis of the isolated "(S)-Compound A".(S)-N-[(4-methoxyphenyl)sulfonyl]-glutamic acid salt gave a diastereomeric purity of at least 99.1 over 0.9 or better.

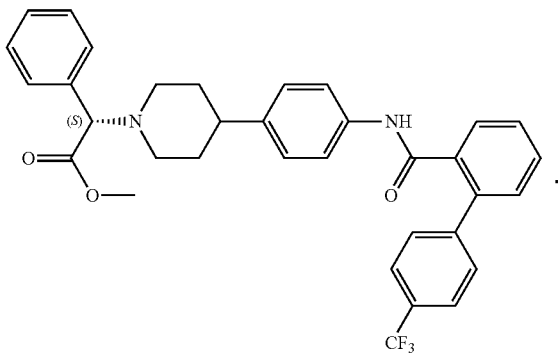

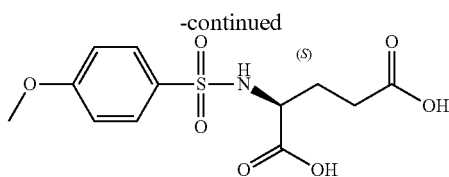

"(S)-Compound A".(S)-N-[(4-methoxyphenyl)sulfonyl]glutamic acid salt

EXAMPLE 3

"(S)-Compound A".(S)-N-[(4-methoxyphenyl)sulfonyl] glutamic acid salt (1 mol) is dissolved in propyleneglycol-monomethylether (6000 ml) and the mixture is heated to a temperature between 55° C. and 60° C. Then an aqueous solution of $Na_2CO_3$ (1.05 mol) in water (600 ml) is added slowly over a period of 20 minutes. The mixture is stirred for an additional 15 minutes and water (1800 ml) is added at a temperature between 50° C. to 55° C. over a period of 30 minutes. After stirring for 1 hour at 50° C., the mixture is cooled to 20° C. and stirred for 12 hours. The precipitate was filtered off and washed with water (860 ml). The product was dried in vacuum, yielding 540 g of "(S)-Compound A".

HPLC analysis of the isolated "(S)-Compound A" gave an enantiomeric ratio of at least 99.1 over 0.9 or better.

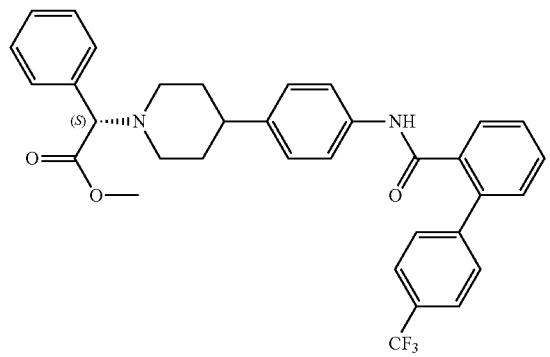

methyl (2S)-phenyl[4-[4-[[[4'-(trifluoromethyl)-2-biphenylyl]carbonyl]amino]phenyl]-1-piperidinyl]acetate

EXAMPLE 4

The filtrate of Example 2 that was set aside was heated till reflux in a reactor and the solvent was partially removed by evaporation till a concentration of "(R)-Compound A".(S)-N-[(4-methoxyphenyl)sulfonyl]glutamic acid salt of 22-27 w/w % in MEK was reached. The reactor was then closed and heated to a temperature of 100° C. (inside pressure was 3.5 to 4 bar (=350 kPa to 400 kPa) and stirred for 4 hours before it was cooled to 58° C. Analysis of the reaction mixture demonstrated the presence of equimolar amounts of "(R)-Compound A".(S)-N-[(4-methoxyphenyl)sulfonyl]glutamic acid salt and "(S)-Compound A".(S)-N-[(4-methoxyphenyl)sulfonyl]glutamic acid salt. Subsequently, the now obtained "(±)-Compound A".(S)-N-[(4-methoxyphenyl)sulfonyl]-glutamic acid salt was then subjected to the procedure of Example 2 and Example 3 in order to obtain "(S)-Compound A".

EXAMPLE 5

Different organic solvents have been evaluated to determine yield and stereomeric purity of the diastereomeric salt "(S)-Compound A".(S)-N-[(4-methoxyphenyl)sulfonyl]-glutamic acid.

A mixture of "(±)-Compound A" (1 mol) and (S)-N-[(4-methoxyphenyl)sulfonyl]glutamic acid (1 mol) in an organic solvent was warmed until a homogenous solution was obtained. The mixture was allowed to cool to 23° C. over 16 hours. The precipitate was filtered and washed with the organic solvent. The yield and diastereomeric ratio of the isolated "(S)-Compound A".(S)-N-[(4-methoxyphenyl)sulfonyl]glutamic acid for different solvents is listed in the Table 1 below using the following analytical method.

Analytical method:
Column: DAICEL Chiralpak AD-RH 150×4.6 mm ID, 5 μm particle size+guardcolumn 10×4.0 mm ID
Mobile phase: solvent A: 20 mM $NH_4HCO_3$+0.1% (v/v) diethylamine in water solvent B: ethanol
Elution mode: isocratic

|  | time (minutes) | |
|---|---|---|
|  | 0 | 15 |
| % A % B | 20 80 | 20 80 |

Total analysis time: 15 minutes
Flow: 1.0 ml/min
Temperature: 35° C.
Injection volume: 10 μl
Detector: wavelength: 245 nm

TABLE 1 yield and optical purity of the precipitated "(S)-Compound A". (S)-N-[(4-methoxyphenyl)sulfonyl]glutamic acid

| solvent (concentration of "(±)-Compound A") | yield (%) | optical yield (%) | diastereomeric ratio |
|---|---|---|---|
| MIK (4 L per mol) | 51.2 | 86.1 | 84.1:15.9 |
| MIK (5 L per mol) | 39.1 | 73.2 | 93.6:6.2 |
| MEK (5 L per mol) | 42 | 82.9 | 98.7:1.3 |
| MEK (3 L per mol) | 38 | 74.1 | 97.5:2.5 |
| 1-propanol (3 L per mol) | 49.4 | 86.5 | 87.6:12.4 |
| 1-propanol (6 L per mol) | 91.0 | 91.0 | 92.1:7.9 |
| ethyl acetate (5 L per mol) | 49.8 | 91.0 | 91.4:8.6 | yield (%): ratio of the isolated precipitate over the amount of starting materials (in this case 1 mol of "(±)-Compound A") in the crystallisation procedure
optical yield (%): ratio of the isolated "(S)-Compound A". (S)-N-[(4-methoxyphenyl)sulfonyl]glutamic acid over its starting amount in the procedure
diastereomeric ratio: the ratio of the percentage of diastereomeric salt "(S)-Compound A".(S)-N-[(4-methoxyphenyl) sulfonyl]glutamic acid over the percentage of the diastereomeric salt "(R)-Compound A".(S)-N—[(4-methoxyphenyl)sulfonyl]glutamic acid

The invention claimed is:

1. A process for isolating methyl (2S)-phenyl[4-[4-[[[4'-(trifluoromethyl)-2-biphenylyl]carbonyl]amino]phenyl]-1-piperidinyl]acetate or a pharmaceutically acceptable salt thereof from (±)-methyl phenyl[4-[4-[[[4'-(trifluoromethyl)-2-biphenylyl]carbonyl]amino]phenyl]-1-piperidinyl]acetate or an acid addition salt thereof comprising the consecutive steps of
    a) mixing (±)-methyl phenyl[4-[4-[[[4'-(trifluoromethyl)-2-biphenylyl]carbonyl]-amino]phenyl]-1-piperidinyl]acetate or an acid addition salt thereof with a suitable amount of (S)-N-[(4-methoxyphenyl)sulfonyl]glutamic acid or an alkali or earth alkaline metal salt thereof in a suitable solvent at an elevated temperature;
    b) cooling the mixture of step a) and collecting the precipitated methyl (2S)-phenyl[4-[4-[[[4'-(trifluoromethyl)-2-biphenylyl]carbonyl]amino]phenyl]-1-piperidinyl] acetate (S)-N-[(4-methoxyphenyl)sulfonyl]glutamic acid salt and setting aside the filtrate comprising methyl (2R)-phenyl[4-[4-[[[4'-(trifluoromethyl)-2-biphenylyl] carbonyl]amino]-phenyl]-1-piperidinyl]acetate (S)—N-[(4-methoxyphenyl)sulfonyl]glutamic acid salt; and
    c) liberating methyl (2S)-phenyl[4-[4-[[[4'-(trifluoromethyl)-2-biphenylyl]carbonyl]-amino]phenyl]-1-piperidinyl]acetate from the said precipitated salt;
    and optionally converting methyl (2S)-phenyl[4-[4-[[[4'-(trifluoromethyl)-2-biphenylyl]carbonyl]amino]phenyl]-1-piperidinyl]acetate into a pharmaceutically acceptable salt.

2. The process as claimed in claim 1 wherein the suitable solvent in step a) is selected from 2-butanone, 4-methyl-2-pentanone, ethyl acetate and 1-propanol, or mixtures thereof.

3. The process as claimed in claim 2 wherein the suitable solvent in step a) is 2-butanone.

4. The process as claimed in claim 3 wherein step a) is carried out at a temperature ranging from 60 to 65° C.

5. The process as claimed in claim 4 wherein the mixture in step b) is cooled according to a non-linear cooling profile.

6. The process as claimed in claim 5 wherein the cooling profile comprises cooling to 55° C. over 15 minutes, to 17.5° C. over 4 hours and to 17° C. over a period of 1 hour to 16 hours.

7. The process as claimed in claim 1 wherein the molar ratio of the amount of (S)-N—[(4-methoxyphenyl)sulfonyl] glutamic acid to the amount of (±)-methyl phenyl[4-[4-[[[4'-(trifluoromethyl)-2-biphenylyl]carbonyl]amino]phenyl]-1-piperidinyl]acetate ranges from 0.5 to 1.1.

8. The process as claimed in claim 7 wherein the molar ratio is 1.05.

9. The process as claimed in claim 1 wherein the (S)-N-[(4-methoxyphenyl)sulfonyl]-glutamic acid salt of methyl (2S)-phenyl[4-[4-[[[4'-(trifluoromethyl)-2-biphenylyl]-carbonyl]amino]phenyl]-1-piperidinyl]acetate is converted into its free base form in step c) by dissolving said salt in an organic solvent at an elevated temperature, followed by the addition of an aqueous solution containing an inorganic or organic base, cooling of the resulting reaction mixture and collecting the precipitated methyl (2S)-phenyl[4-[4-[[[4'-(trifluoromethyl)-2-biphenylyl]carbonyl]amino]-phenyl]-1-piperidinyl]acetate.

10. The process as claimed in claim 9 wherein the organic solvent is propyleneglycol-monomethylether.

11. The process as claimed in claim 1 wherein the methyl (2R)-phenyl[4-[4-[[[4'-(trifluoromethyl)-2-biphenylyl]carbonyl]amino]-phenyl]-1-piperidinyl]acetate.(S)-N—[(4-methoxyphenyl)sulfonyl]glutamic acid salt present in the filtrate that was set aside in step b) is epimerised into (±)-methyl phenyl[4-[4-[[[4'-(trifluoromethyl)-2-biphenylyl]carbonyl] amino]-phenyl]-1-piperidinyl]acetate.(S)-N-[(4-methoxyphenyl)sulfonyl]glutamic acid salt.

12. The process as claimed in claim 11 wherein the epimerisation is performed by heating the filtrate at an elevated temperature for a prolonged time, optionally at an increased pressure.

13. The process as claimed in claim 12 wherein the epimerisation is performed at a temperature of 100° C. at a pressure between 350 kPa to 400 kPa.

* * * * *